United States Patent [19]

Miyajima et al.

[11] 4,287,102
[45] Sep. 1, 1981

[54] DETERGENT COMPOSITION

[75] Inventors: Nobuyuki Miyajima, Tokyo; Nobuo Johna, Funabashi; Naoki Mizushima, Ichikawa; Kazuo Ohbu, Tokyo, all of Japan

[73] Assignee: The Lion Fat & Oil Co., Ltd., Tokyo, Japan

[21] Appl. No.: 131,636

[22] Filed: Mar. 19, 1980

[30] Foreign Application Priority Data

Oct. 11, 1979 [JP] Japan .................. 54-131198

[51] Int. Cl.³ .................. C11D 1/14; C11D 1/83
[52] U.S. Cl. .................. 252/547; 252/545; 252/555
[58] Field of Search .................. 252/545, 547, 555

[56] References Cited

U.S. PATENT DOCUMENTS

| 3,086,943 | 4/1963 | Lang | 252/547 X |
| 3,332,875 | 7/1967 | Kessler et al. | 252/545 X |
| 3,808,156 | 4/1974 | Gorisch et al. | 252/545 |
| 3,928,249 | 12/1975 | Nunziata et al. | 252/526 |
| 3,943,234 | 3/1976 | Roggenkamp | 424/343 |
| 3,979,340 | 9/1976 | Klisch et al. | 252/548 |
| 3,980,588 | 9/1976 | Rubinfeld | 252/548 |
| 4,003,857 | 1/1977 | Gorisch et al. | 252/546 |
| 4,064,076 | 12/1977 | Klisch et al. | 252/542 |

FOREIGN PATENT DOCUMENTS

| 938988 | 10/1963 | United Kingdom | 252/547 |
| 1082076 | 9/1967 | United Kingdom | 252/547 |
| 1524441 | 9/1978 | United Kingdom . | |

Primary Examiner—P. E. Willis, Jr.
Attorney, Agent, or Firm—Armstrong, Nikaido, Marmelstein & Kubovcik

[57] ABSTRACT

A detergent composition, suitable for use in washing vegetables and dishes and shampooing human hair, having both good detergency and little hand roughening action is presented. This detergent composition contains:

(a) a water-soluble salt of olefin sulfonic acid having 12 to 16 carbon atoms and
(b) a tertiary amine oxide having the formula

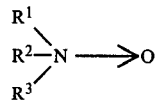

wherein $R^1$ is an alkyl group of 10 to 14 carbon atoms, and $R^2$ and $R^3$ are independently an alkyl or hydroxyalkyl group, of 1 to 3 carbon atoms. The contents of each of said components (a) and (b) in the composition being within the range of from 2 to 20% by weight, and the mol ratio of the component (a) to the component (b) being within the range of from 1.5/1 to 0.5/1, and the pH of an aqueous solution of the detergent composition being within the range of from 7.3 to 8.0 at the concentration when it is used in washing vegetables and dishes.

4 Claims, No Drawings

DETERGENT COMPOSITION

This invention relates to detergent compositions suitable for use in washing vegetables and dishes or shampooing human hair. More specifically, it relates to detergent compositions having both excellent detergent characteristics or detergency and little hand roughening action.

Conventional detergent compositions heretofore used for washing vegetables and dishes usually contain, as a main ingredient, anionic surface active agents such as linear alkylbenzene sulfonates, alkyl sulfates, alkylethoxy sulfates and the like. However, these conventional detergent compositions have the disadvantage that, when they are used for the hand washing of, for example, vegetables and dishes, the skin on the hands becomes rough and unsightly. That is to say, since said anionic surface active agents have a strong detergency, they tend to simultaneously remove the sebum from human skin together with the soil from materials being washed. It is believed that this degreasing activity causes such hand roughening.

Under these circumstances, various proposals have been made in the prior arts to develop detergent compositions for washing vegetables and dishes having little hand roughening action. For instance, fatty acid type surface active agents, having a minor degreasing action but having detergency less than that of said anionic surface active agents, are used as a main ingredient of the conventional detergent compositions; or oils and proteins are incorporated into the detergent compositions to suppress their degreasing activity. However, the existing prior arts still do not satisfactorily meet the present demand for liquid detergent compositions, for washing vegetables and dishes or shampooing human hair, having both good detergency and little or no hand roughening action.

Accordingly, an object of this invention is to obviate the aforementioned problem of the prior arts and to provide a detergent composition, suitable for use in washing vegetables and dishes and in shampooing human hair, having both good detergency and little hand roughening action.

Other objects and advantages of this invention will be apparent from the description set forth hereinbelow.

In accordance with this invention, there is provided a detergent composition comprising:

(a) at least one water-soluble salt of olefin sulfonic acid having 12 to 16 carbon atoms and (b) at least one tertiary amine oxide having the formula

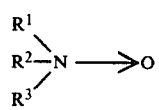

wherein $R^1$ is an alkyl group of 10 to 14 carbon atoms, and $R^2$ and $R^3$ are independently an alkyl or hydroxyalkyl group, of 1 to 3 carbon atoms, the content of each of said components (a) and (b) in the composition being within the range of from 2 to 20% by weight, and the mol ratio of the component (a) to the component (b) being within the range of from 1.5/1 to 0.5/1, and the pH of an aqueous solution of the detergent composition being within the range of from 7.3 to 8.0 at the concentration to be used in washing.

The present inventors found, after extensive study of hand roughening caused by the use of detergent compositions, that there is a close correlation between the hand roughening phenomenon and the structure of proteins in skin. That is to say, hand roughening is caused by the denaturation of proteins due to the adsorption and bonding, to the proteins in skin, of the anionic surface active agents present in the conventional detergent compositions, rather than caused by the degreasing of sebum. Based on this finding the present inventors then conducted studies to develop detergent compositions having both good detergency and little hand roughening action. In these studies, the phenomenon of the protein denaturation was used as an indicator of the hand roughening. As a result, the inventors found that detergent compositions having both good detergency and little hand roughening action can be obtained by (i) using water-soluble salts of olefin sulfonic acids, which are anionic surface active agents, in combination with tertiary amine oxides, which are semi-polar nonionic surface active agents, in a specified ratio and (ii) adjusting the pH of the liquid detergent compositions to the specified range during their use in washing vegetables and dishes or shampooing human hair.

The component (a) (i.e. water-soluble salts of olefin sulfonic acid having 12 to 16 carbon atoms) used in this invention, can be prepared, in any conventional manner, from a starting olefin or olefins having 12 to 16 carbon atoms. For instance, after sulfonating the starting olefin by a thin-film type sulfonation method, the sulfonated products are neutralized with an appropriate basic substance, for example, alkali metal hydroxides, such as sodium hydroxide, potassium hydroxide and the like, alkaline earth metal hydroxides, such as magnesium hydroxide and the like, aqueous ammonia and alkanol amines, such as monoethanol amine and triethanol amine and; then, the neutralized products are hydrolyzed at a temperature of from 100° to 200° C. to form the water-soluble salts of the alpha-olefin sulfonic acids having 12 to 16 carbon atoms. When the component (a) is desired to be obtained as a magnesium salt, it may also be prepared by first preparing sodium olefin sulfonate followed by the metathetical reaction thereof with an equivalent amount of, for example, magnesium sulfate.

As the starting material, there may advantageously be employed alpha-olefins, including vinylidene type olefins, which can be prepared by, for example, a wax cracking process, an ethylene polymerization process using a Ziegler-Natta catalyst or modified processes thereof. Inner olefins, derived from the dehydrogenation of n-paraffins or the dehydrochlorination of the chlorinated n-paraffins, may also be used as the starting material.

The water-soluble salts of olefin sulfonates may be used alone or in any combination thereof in the detergent composition of this invention. However, the detergent composition of this invention preferably contains at least 50% by weight of, based on the total amount of the component (a), the water-soluble salt or salts of olefin sulfonic acid or acids having 14 carbon atoms, since the detergency becomes insufficient.

The component (b) of this invention is tertiary amine oxides having the following formula.

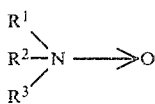

wherein $R^1$ is an alkyl group of 10 to 14 carbon atoms, and $R^2$ and $R^3$ are independently an alkyl or hydroxyalkyl group of 1 to 5 carbon atoms. Typical examples of such alkylamine oxides used, as the component (b), in this invention are dimethyldecylamine oxide, dimethyltetradecylamine oxide, bis(2-hydroxyethyl)dodecylamine oxide, dimethyldodecylamine oxide and the like. These tertiary amine oxides may be used alone or in any combination thereof in the detergent composition of this invention. However, the detergent composition of this invention preferably contains at least 90% by weight of, based on the total amount of the component (b), the tertiary amine oxide having an alkyl group of 12 carbon atoms.

As mentioned hereinabove, the following three requirements, i.e. the amounts of the components (a) and (b) in the composition, the mol ratio of the component (a) to the component (b) in the composition and the pH of an aqueous solution of the detergent composition during its use in washing vegetables and dishes or shampooing human hair, are essential for the detergent composition of this invention:

(1) the content of each of the components (a) and (b) in the composition should be within the range of from 2 to 20% by weight. (Preferable total amount of the components (a) and (b) in the detergent composition is within the range of from 6 to 30% by weight.)

(2) The mol ratio of the component (a) to the component (b) in the composition should be within the range of from 1.5/1 to 0.5/1.

(3) The pH of an aqueous solution of the detergent composition at the concentration to be used in the washing (e.g. approximately 0.2% by weight) should be within the range of from 7.3 to 8.0.

Unless all these requirements are fulfilled, the desired detergent composition having both good detergency and little hand roughening action cannot be obtained. Although the detailed mechanism cannot be clearly understood at present, it is believed that the olefin sulfonates and the semi-polar nonionic surface active agents (i.e. tertiary amine oxides) form complex micelle in an aqueous detergent solution or wash liquor and, therefore, the micelle charge becomes small compared to that composed of the olefin sulfonates so that substantial denaturation of the proteins in the skin does not occur. In order to form the complex micelle in the wash liquor, the mol ratio of the olefin sulfonate to the amine oxide and the pH of the wash liquor should be limited to the ranges specified above. Thus, only when the afore-mentioned three requirements (1), (2) and (3) are fulfilled, the detergent composition having both good detergency and little roughening action can be obtained.

In the case where the content of the component (a) or (b) in the composition is less than 2% by weight, the detergency becomes insufficient. Contrary to this, in the case where the content of the component (a) or (b) in the composition is more than 20% weight, the viscosity of composition becomes higher and a large amount of hydrotrope is needed to reduce the viscosity.

In the case where the mol ratio of the component (a) to the component (b) is more than 1.5/1, both the protein denaturation and the inhibition of enzyme activity are caused. Contrary to this, in the case where the mol ratio of the component (a) to the component (b) is less than 0.5/1, the detergency becomes insufficient.

In the case where the pH of an aqueous detergent solution during the use thereof in the washing is less than 7.3, the detergency becomes insufficient. Contrary to this, in the case where the pH of an aqueous detergent solution during the use thereof in the washing is more than 8.0, both the protein denaturation and the inhibition of enzyme activity are caused.

The mixing of the component (a) and the component (b) can be carried out in any conventional manner. These components (a) and (b) can be advantageously combined with each other, both in the form of aqueous solutions in such a manner that the formed detergent composition satisfies the aforemetnioned three requirements. The pH of the aqueous detergent solution can be easily adjusted by the addition of acids or basic substances.

So long as the above-mentioned requirements are satisfied, other conventional additives, such as nonionic surface active agents, amphoteric surface active agents, hydrotropes and the like, can be incorporated into the detergent compositions according to this invention. Typical examples of such nonionic surface active agents are coconut fatty acid monoethanol amides, coconut fatty acid diethanol amides, alcohol ethoxylates derived from an addition reaction of from 5 to 20 mol, on the average, of ethylene oxide to alcohols having 8 to 16 carbon atoms; alkylphenol ethoxylates derived from an addition reaction of from 5 to 10 mol, on the average, of ethylene oxide to alkyl phenols having alkyl groups of 8 to 11 carbon atoms and the like. Examples of amphoteric surface active agents optionally employed in this invention are betaine, sulfobetaine, imidazoline and the like. As the hydrotropes, xylene sulfonates, benzene sulfonates, polyethylene glycol, polypropylene glycol, ethylene glycol, glycerine, sorbitol, ethanol, propanol and the like can be optionally used in this invention. Other additives which can be used in this invention are, for example, potassium chloride, potassium sulfate, ammonium chloride, ammonium sulfate, sodium benzoate, ethylenediamine tetraacetate and the like. Various perfumes can also be incorporated into the detergent composition of this invention.

This invention now will be further illustrated by, but is by no means limited to, the following Examples.

EXAMPLE 1

Each liquid detergent composition having the composition listed in Table 1 below was prepared by mixing the components listed in Table below with each other with stirring.

The detergent power or detergency and the degree of the protein denaturation of each liquid detergent composition were evaluated. The degree of the protein denaturation was evaluated by determining the molar ellipticity of bovine serum albumin and the inhibition rate of the enzyme activity of tyrosinase, which has a close correlation with clinical hand roughening results. The results are also shown in Table 1 below.

[Test Method]

(1) Detergency 10 g each of pharmacopoeia soybean oil and pharmacopoeia tallow are added to 60 ml of chloroform, and 0.1 g of Oil Red is then added to the mixture with stirring to prepare a soil or stain solution. A group of six glass plates are soiled by the solution prepared above and are then allowed to stand for 30 minutes at 25° C. Thereafter, these soiled glasses are washed in 700 ml of a detergent solution (i.e. wash liquor) for 3 minutes at an agitation speed of 250 rpm, followed by washing with water for 1 minute. Then the washed glasses are air dried. Measuring the weight of oil before washing and after washing, the detergency is calculated by the following formula.

$$\text{Detergency (\%)} = \frac{A - B}{A} \times 100$$

A: weight of oil before washing
B: weight of oil after washing.

(2) Molar ellipticity of Bovine Serum Albumin (BSA Molecular Eliptic Rate)

After mixing 100 ppm of bovine serum albumin with each detergent composition, a buffer solution of sodium phosphate is added in such an amount that the concentration thereof in the mixture becomes 50 mM. The circular dichroism of the mixture is measured at 25° C. by using JASCO CD Spectropolarimeter and the molar ellipticity [θ] is determined. The molar ellipticity of the non-denatured bovine serum albumin was $-11.3 \times 10^6$ deg cm²/decimol. The results shown in the Tables below in terms of $-[\theta] \times 10^{-6}$.

(3) Inhibition Rate of Enzymic Activity

10 μg of tyrosinase is added to 2.5 ml of 0.2% aqueous detergent solution and is allowed to stand for 30 minutes at 37° C. Then, 1.0 ml of an aqueous buffer solution containing 1.5 ml of 0.1 M sodium phosphate buffer solution and 3 mg of dihydroxyphenyl alanine is added to the solution with stirring and the absorbance thereof at 475 nm is measured. The inhibition rate of enzymic activity of the detergent solution is determined from the difference in the absorbance between a sample and a blank (which contains no active agent). Detergent compositions having an inhibition rate of the enzymic activity of 5% or less are good.

As is clear from the results shown in Table 1 below, the detergent compositions according to this invention of Run Nos. 1, 2 and 3 have both good detergency and little hand roughening action.

TABLE 1

| Run No. | 1 | 2 | 3 | 4* | 5* | 6* | 7* |
|---|---|---|---|---|---|---|---|
| Composition (wt %) | | | | | | | |
| Sodium C₁₄ alpha-olefin sulfonate (AOS) | 13.3 | 10 | 8 | 20 | 16 | 4 | 0 |
| Dodecyldimethylamine oxide | 6.7 | 10 | 12 | 0 | 4 | 16 | 20 |
| Coconut fatty acid diethanol amide | 3 | 3 | 3 | 3 | 3 | 3 | 3 |
| Sulfuric acid | 0.4 | 0.6 | 0.5 | — | 0.25 | 0.25 | — |
| Ethanol | 5 | 5 | 5 | 5 | 5 | 5 | 5 |
| Water | Balance | Balance | Balance | Balance | Balance | Balance | Balance |
| AOS/amine oxide (mol ratio) | 1.5/1 | 0.76/1 | 0.5/1 | — | 3/1 | 0.19/1 | — |
| pH of 0.2% aqueous solution at 25° C. | 7.5 | 7.5 | 7.5 | 7.5 | 7.5 | 7.5 | 7.5 |
| Properties | | | | | | | |
| BSA molar ellipticity-[θ] × 10⁻⁶ | 11.3 | 11.3 | 11.3 | 9.0 | 9.7 | 11.3 | 11.3 |
| Inhibition Rate of Enzyme Activity (%) | 3 | 1 | 2 | 25 | 10 | 6 | 7 |
| Detergency | 65 | 55 | 50 | 7 | 70 | 20 | 1 |

*Comparative Examples

EXAMPLE 2

Various detergent compositions having the compositions listed in Table 2 below were prepared in a manner as described in Example 1. The properties of these detergent compositions were determined in a manner as described in Example 1. The results are shown in Table 2.

As is clear from the results shown in Table 2, the detergent compositions of this invention of Run Nos. 8, 9 and 10 have both good detergency and little hand roughening action.

EXAMPLE 3

Various detergent compositions, having the compositions listed in Table 3 below, were prepared in a manner as described in Example 1, except that the mixtures of sodium C₁₂, C₁₄ and C₁₆ alpha-olefin sulfonates were used as AOS. The properties of these detergent compositions were determined in a manner as described in Example 1. The results are shown in Table 3 below.

As is clear from the results shown in Table 3, the detergent compositions of this invention of Run Nos. 14 through 18 have both good detergency and little skin roughening action.

TABLE 2

| Run No. | 8 | 9 | 10 | 11* | 12* | 13* |
|---|---|---|---|---|---|---|
| Composition | | | | | | |
| Sodium C₁₄ alpha-olefin sulfonate (AOS) | 10 | 10 | 10 | 10 | 10 | 10 |
| Dodecyldimethylamine oxide | 10 | 10 | 10 | 10 | 10 | 10 |
| Coconut fatty acid diethanol amine | 3 | 3 | 3 | 3 | 3 | 3 |
| Sulfuric acid | 0.7 | 0.6 | 0.5 | 1.5 | 0.8 | 0.03 |
| Ethanol | 5 | 5 | 5 | 5 | 5 | 5 |
| Water | Balance | Balance | Balance | Balance | Balance | Balance |
| AOS/amine oxide (mol ratio) | 0.76/1 | 0.76/1 | 0.76/1 | 0.76/1 | 0.76/1 | 0.76/1 |
| pH of 0.2% aqueous solution at 25° C. | 7.3 | 7.7 | 8.0 | 6.5 | 7.0 | 8.5 |
| Properties | | | | | | |
| BSA molar ellipticity-[θ] × 10⁻⁶ | 11.3 | 11.3 | 11.3 | 11.3 | 11.3 | 10.5 |
| Inhibition Rate of Enzyme activity (%) | 2 | 2 | 3 | 4 | 2 | 10 |
| Detergency | 50 | 60 | 65 | 0 | 3 | 65 |

*Comparative Examples

TABLE 3

| Run No. | 14 | 15 | 16 | 17 | 18 |
|---|---|---|---|---|---|
| Composition | | | | | |
| Sodium $C_{12}$ alpha-olefin sulfonate | 5 | — | 1 | 8 | — |
| Sodium $C_{14}$ alpha-olefin sulfonate | 5 | 5 | 8 | 2 | 3 |
| Sodium $C_{16}$ alpha-olefin sulfonate | — | 5 | 1 | — | 7 |
| Dodecyldimethylamine oxide | 10 | 10 | 10 | 10 | 10 |
| Citric acid | 0.5 | 0.5 | 0.5 | 0.5 | 0.5 |
| Ethanol | 5 | 5 | 5 | 5 | 5 |
| Coconut fatty acid diethanol amide | 3 | 3 | 3 | 3 | 3 |
| Water | Balance | Balance | Balance | Balance | Balance |
| AOS/amine oxide (mol ratio) | 0.79/1 | 0.72/1 | 0.76/1 | 0.82/1 | 0.71/1 |
| pH of 0.2% aqueous solution (25° C.) | 7.5 | 7.5 | 7.5 | 7.5 | 7.5 |
| Properties | | | | | |
| BSA molar ellipticity-$[\theta] \times 10^{-6}$ | 11.3 | 11.3 | 11.3 | 11.3 | 11.3 |
| Inhibition Rate of Enzyme Activity (%) | 2 | 3 | 2 | 2 | 0 |
| Detergency | 50 | 55 | 55 | 40 | 45 |

We claim:
1. A detergent composition comprising:
   (a) at least one water-soluble salt of olefin sulfonic acid having 12 to 16 carbon atoms and
   (b) at least one tertiary amine oxide having the formula

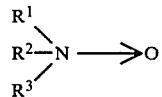

wherein $R^1$ is an alkyl group of 10 to 14 carbon atoms, and $R^2$ and $R^3$ are independently an alkyl or hydroxyalkyl group of 1 to 3 carbon atoms, the content of each of said components (a) and (b) in the composition being within the range of from 2 to 20% by weight, and the mol ratio of the component (a) to the component (b) being within the range of from 1.5/1 to 0.5/1 and the pH of an aqueous solution of the detergent composition at a concentration of about 0.2% by weight being within the range of from 7.3 to 8.0.

2. A detergent composition as claimed in claim 1, wherein at least 50% by weight of the component (a) is the water-soluble salt of olefin sulfonic acid having 14 carbon atoms.

3. A detergent composition as claimed in claim 1, wherein at least 90% by weight of the component (b) is the tertiary amine oxide having an alkyl group of 12 carbon atoms.

4. A detergent composition as claimed in claim 1, wherein the total amount of the components (a) and (b) in the detergent composition is within the range of from 6 to 30% by weight.

* * * * *